(12) United States Patent
Hanna

(10) Patent No.: US 6,302,911 B1
(45) Date of Patent: Oct. 16, 2001

(54) INTRAOCULAR IMPLANT WITH GUTTER SHAPED HAPTIC

(75) Inventor: Khalil Hanna, Paris (FR)

(73) Assignee: Humanoptics AG, Erlangen (DE)

( * ) Notice: Subject to any disclaimer, the term of this patent is extended or adjusted under 35 U.S.C. 154(b) by 0 days.

(21) Appl. No.: 09/692,719

(22) Filed: Oct. 20, 2000

(30) Foreign Application Priority Data

Oct. 21, 1999 (FR) .................................. 99 13125

(51) Int. Cl.[7] .................................................. A61F 2/16
(52) U.S. Cl. .......................................... 623/6.39; 623/6.54
(58) Field of Search .................... 623/6.45–6.55, 623/6.39–6.44, 6.11, 6.16, 6.17

(56) References Cited

U.S. PATENT DOCUMENTS

| | | | |
|---|---|---|---|
| 3,994,027 | * | 11/1976 | Jensen et al. ............................. 3/13 |
| 4,718,905 | * | 1/1988 | Freeman .................................. 623/6 |
| 6,152,959 | * | 11/2000 | Portney ................................ 623/6.51 |
| 6,159,242 | * | 12/2000 | Yamasita et al. ..................... 623/6.46 |

FOREIGN PATENT DOCUMENTS

| | | |
|---|---|---|
| A1-2728458 | 6/1996 | (FR) . |
| A1-2776181 | 9/1999 | (FR) . |
| A2215076 | 9/1989 | (GB) . |
| A1-9726842 | 7/1997 | (WO) . |

* cited by examiner

Primary Examiner—Corrine McDermott
Assistant Examiner—Hieu Phan

(57) ABSTRACT

An intraocular implant having a single piece having a central optical portion and at least two haptic portions, wherein the free end of each haptic portion is situated on a circle and is shaped to form a gutter.

7 Claims, 2 Drawing Sheets

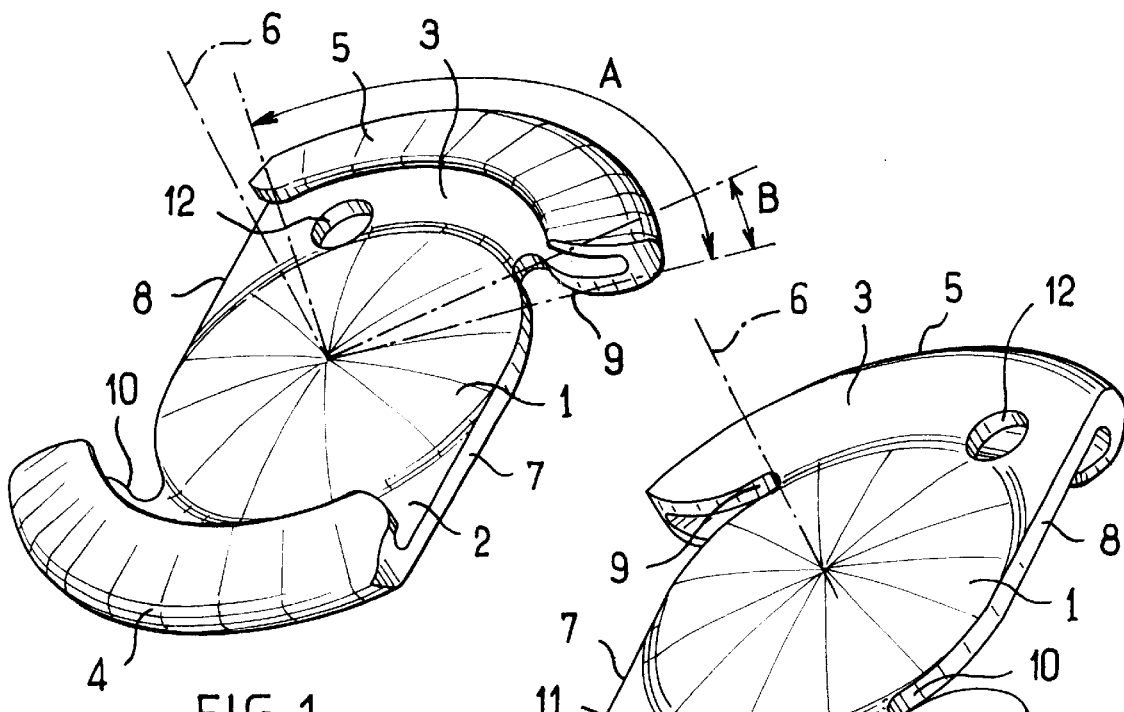
FIG_1
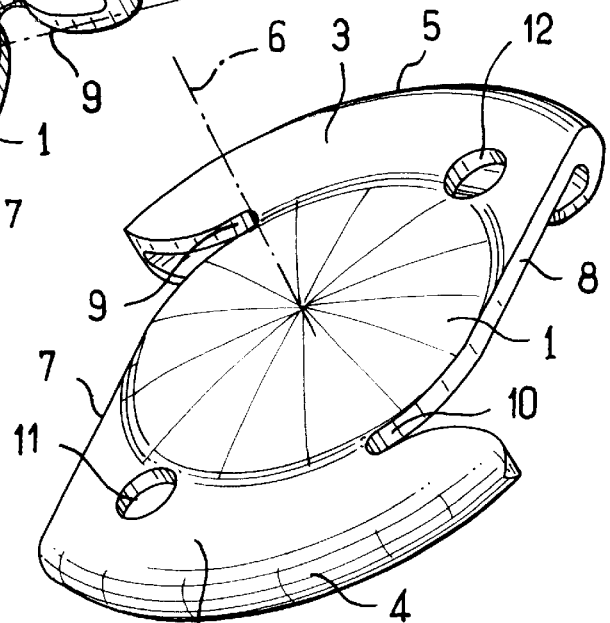
FIG_2
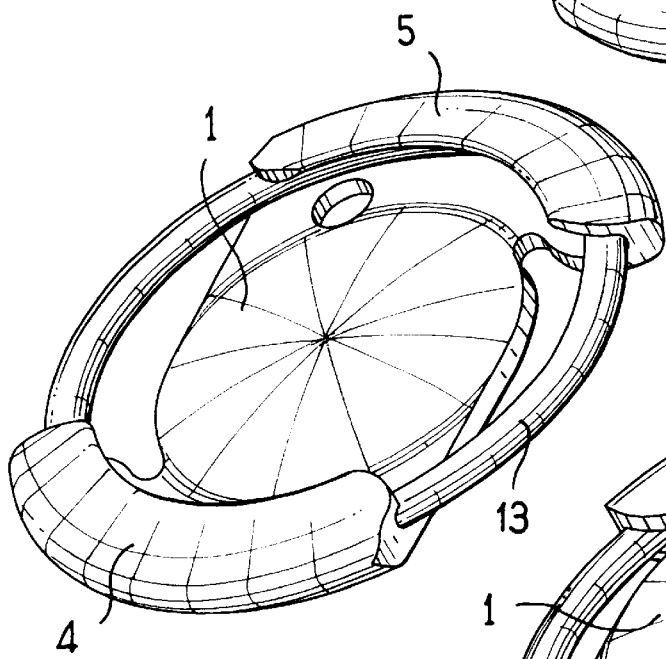
FIG_3
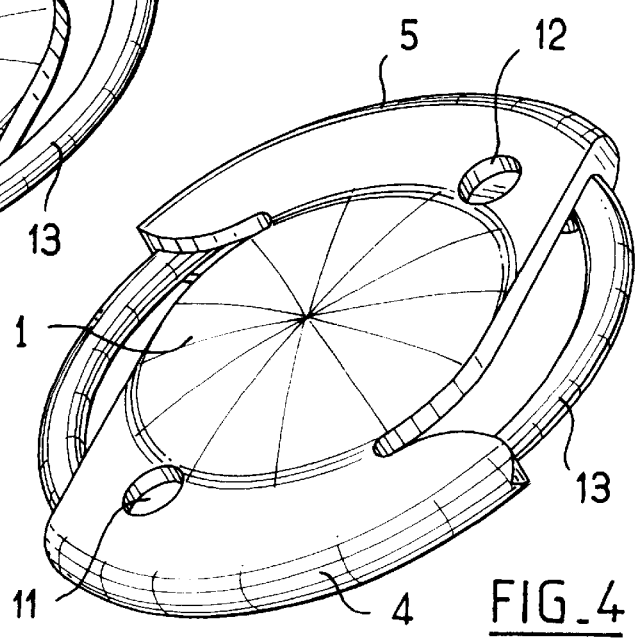
FIG_4

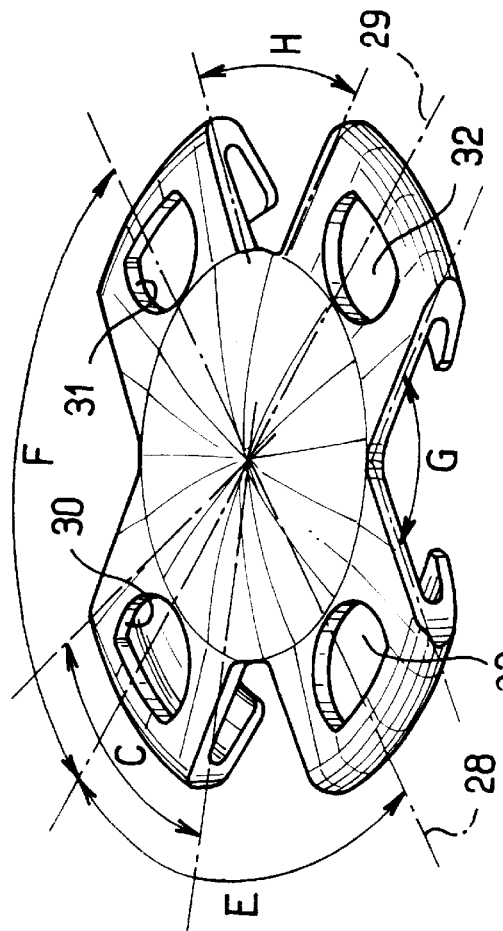
FIG._6
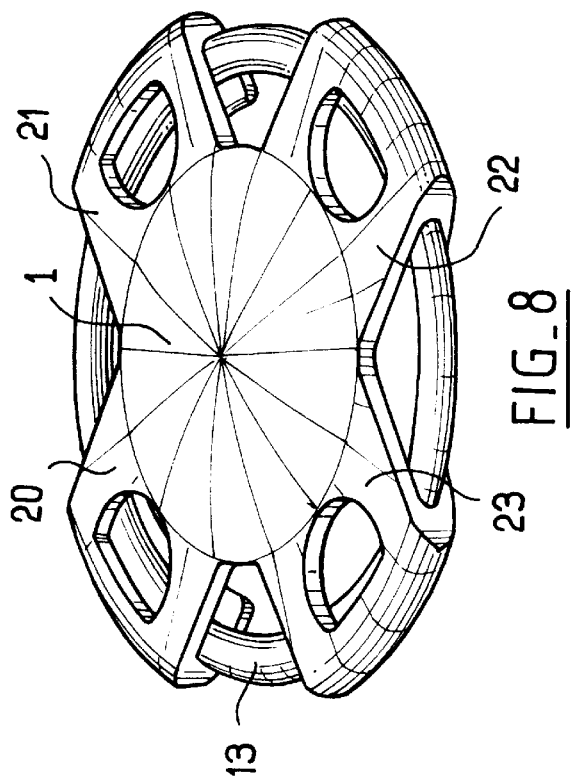
FIG._8
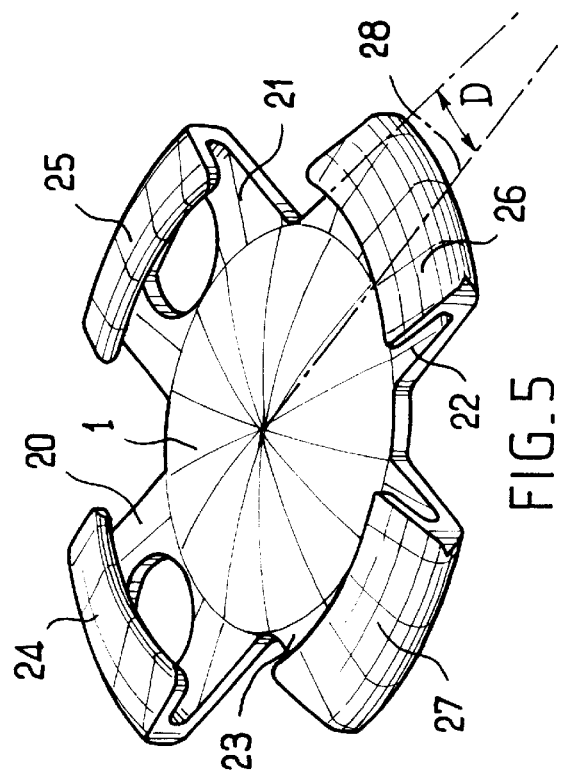
FIG._5
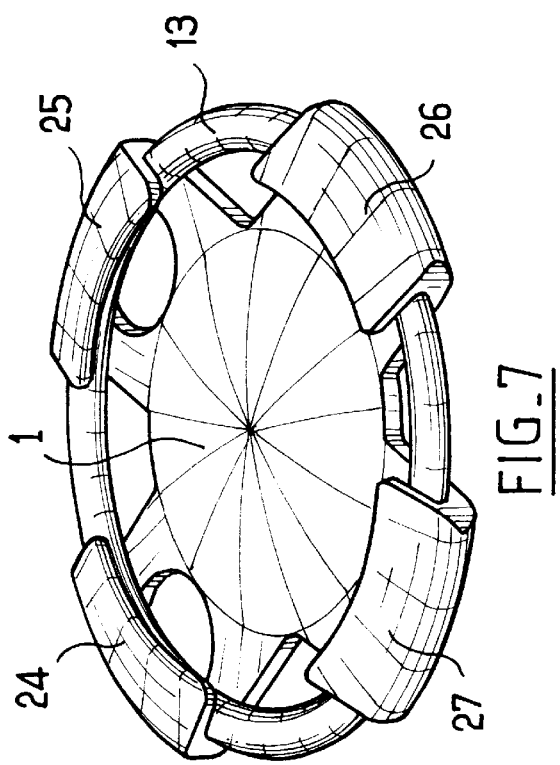
FIG._7

INTRAOCULAR IMPLANT WITH GUTTER SHAPED HAPTIC

The present invention relates to an ocular implant forming an artificial lens to be received in the capsular bag after a cataract operation.

BACKGROUND OF THE INVENTION

One of the numerous techniques in existence for performing the cataract operation, consists in extracting the lens material from the capsular bag after making a circular opening in the anterior wall of the bag (capsulorhexis). The preserved portion of the capsular bag then comprises the posterior wall and a ring of the anterior wall connected to the posterior wall by the equatorial wall of the bag which co-operates with the ciliary muscle via the zonular fibers.

After this lens material has been extracted, artificial lens (an implant) is generally installed in what remains of the capsular bag, the artificial lens comprising a central optical portion fitted with so-called "haptic" portions which serve to hold the optical portion in the capsular bag by bearing against the inside face of the equatorial zone of the capsular bag.

These haptic portions can be of numerous shapes. Among the most common, mention is made of resilient loops which extend radially from the optical portion and then curve so as to present respective relatively long portions that bear resiliently against the inside diameter of the capsular bag. Others are formed by radial arms that are regularly distributed around the optical portion and that terminate in respective outer swellings in the form of circular arcs that bear against the equatorial zone of the bag.

It is known that the presence of the epithelial cells which line the inside surface of the capsular bag in the equatorial zone gives rise to cell growth inside the bag, which growth is referred to as fibrosis. This fibrosis differs very widely from one subject to another and its extent can be estimated by the surgeon during a clinical examination of the patient. In general, it occurs to a greater extent in the equatorial zone of the bag where the germinal cells are located.

One of the consequences of this fibrosis lies in the dislocation or progressive expulsion of the implant from the capsular bag. One of the qualities that an implant needs to present thus lies in its ability to accommodate such fibrosis either in order to limit it or else in order to take advantage of it so as to secure the implant better in the capsular bag.

OBJECTS AND SUMMARY OF THE INVENTION

The implant of the invention offers these qualities, and in addition its structure enables the surgeon to adapt the aptitude of the implant for accommodating the greater or lesser extent of fibrosis as estimated when making a diagnosis.

To this end, the invention thus provides an intraocular implant comprising a single piece having a central optical portion and at least two haptic portions, in which the free end of each haptic portion is situated on a circle and is shaped to form a gutter.

One of the functions of this gutter is to keep the anterior ring that remains after capsulorhexis separate from the posterior wall in the vicinity of the equatorial zone of the capsular bag. This gutter shape makes it possible to preserve sufficient flexibility in the portions of the implant to enable it to be folded easily, thereby facilitating insertion into the eye, which would not be possible with a swelling of the same dimensions. Another advantage of the gutter lies in the possibility of the implant receiving a secondary piece in the form of a ring when the surgeon is of the opinion that a large amount of fibrosis is very probable. The ring serves to limit cell growth and to reinforce the ends of the haptic portions, thereby increasing their ability to withstand thrust from the fibrosis. A solid ring installed in the gutters of all of the haptic portions also makes it possible to reduce the thickness of said haptic portions.

BRIEF DESCRIPTION OF THE DRAWINGS

Other characteristics and advantages of the invention will appear on reading the following description of two embodiments of the invention.

Reference is made to the accompanying drawings, in which:

FIGS. 1 and 2 are two opposite views showing the outside of a first embodiment of the invention;

FIGS. 3 and 4 show a ring installed in the implant shown in FIGS. 1 and 2;

FIGS. 5 and 6 are two opposite views showing the outside of a second embodiment of the implant of the invention; and FIGS. 7 and 8 show the second embodiment of the implant fitted with a reinforcing ring.

MORE DETAILED DESCRIPTION

The implant shown in FIGS. 1 to 4 comprises as a single piece a central optical portion 1 generally in the form of a biconvex lens having a diameter of about 6 mm, for example, and having two diametrically-opposite haptic portions 2 and 3, each terminated by a respective folded-over rim 4, 5 forming a curvilinear gutter-shape, and extending along a circle centered on the axis 6 of the optical portion. By way of example, the outside diameter within which the implant is inscribed is about 10 mm to 10.5 mm, with the bottoms of the gutters extending along a circle which is concentric with the circumscribed circle and having a diameter of about 9 mm to 9.5 mm. Each haptic portion is symmetrical relative to the other about the axis 6 and the angular extent A of each gutter is about 100°. The portion connecting each gutter to the optical portion extends in the midplane of the optical lens 1 and is defined laterally on one side by a respective edge 7, 8 that is tangential to the optical portion, and on the other side by a respective opposite edge 9, 10 which is notched, with the angular depth B of the notch being about 20°. This part of the haptic portion between the optical portion and the gutter has a respective hole 11, 12 which, together with the above-mentioned notches, enables the implant to be turned inside the capsular bag.

The thickness of the implant across the gutters is about 1.5 mm, for example. The thickness of the haptic portions measured in their intermediate parts is about 0.3 mm.

Where necessary, the implant of the invention can also include a generally toroidal ring 13 of elastically deformable material of diameter that matches the gutter-bottom diameter of the implant and that is of substantially circular section of diameter corresponding to the width of the above-mentioned gutters.

The implant is made of a material that is known per se that possesses the optical refractive qualities necessary for forming a lens possessing defined characteristics, and flexibility qualities enabling the implant and the ring to be folded so as to present a small dimension suitable for insertion through a relatively small incision in the eye.

The second embodiment of the implant of the invention as shown in FIGS. 5 and 8 is similar to that described in that it comprises a central optical portion 1 in the form of a biconvex lens, for example, and haptic portions 20, 21, 22, and 23 that are likewise folded-over at their ends to form gutters 24, 25, 26, and 27 that are entirely similar to the gutters 4 and 5 described above. The angular circumferential extent of each haptic portion referenced C in the figures is about 40° in this embodiment, and the link portion connecting each gutter to the central optical portion is defined by two parallel side edges which are inclined at an angle D of about 7° to 8° relative to the middle radius 28 of each gutter.

It will be observed that the four haptic arms of this embodiment are not distributed regularly around the optical portion but form an X-shape. Pairs of opposite haptics lie on respective middle diameters 28 and 29, and the angle at the center formed between these two diameters is about 80° (angle E) or the supplementary angle thereof, i.e. 100° (angle F). Thus, the side edges of two adjacent haptic portions form between them an angle G of about 115° or H of about 65°.

As in the preceding embodiment, each haptic arm possesses a respective hole 30, 31, 32, 33.

The ring 13 described with reference to the preceding figures can likewise be associated with this type of implant as shown in FIGS. 7 and 8. It performs the same function therein.

Finally, the implant of the invention is designed to be implanted in such a manner that the free lips or rims of the gutters face towards the anterior wall of the capsular bag, i.e. the face of the implant that is visible in FIGS. 2, 4, 6, and 8 is the face which is turned towards the posterior wall of the capsule.

What is claimed is:

1. An intraocular implant comprising a single piece having a central optical portion and at least two haptic portions, wherein the free end of each haptic portion is situated on a circle and is shaped to form a gutter.

2. An intraocular implant according to claim 1, wherein each haptic portion has a hole between the gutter and the optical portion.

3. An implant according to claim 1, having two haptic portions disposed symmetrically to each other about the central axis of the optical portion, each having a gutter of angular extent A of about 100°, one lateral edge which is tangential to the optical portion, and another lateral edge which is notched over an angle B of about 20°.

4. An implant according to claim 1, having four haptic portions distributed around the optical portion, each haptic portion extending circumferentially over an angular extent C of about 40° and being defined by two parallel side edges that are inclined relative to the middle radius of their gutter by an angle D of about 7° to 8°.

5. An intraocular implant according to claim 4, wherein the middle radiuses of opposite pairs of haptic portions lie on respective common diameters of the implant, said two diameters intersecting at an angle of about 100° (or 80°) and wherein the edges of two adjacent haptic portions form between them an angle of about 115° (or 65°).

6. An intraocular implant according to claim 1, including an independent, elastically-deformable ring suitable for being received in the gutters of all of the haptic portions.

7. An implant according to claim 1, wherein, when it is received in the capsular bag, the free edges of the gutters are situated beside the anterior wall of the capsular bag.

* * * * *